United States Patent [19]
McNeill et al.

[11] Patent Number: 5,300,496
[45] Date of Patent: Apr. 5, 1994

[54] COMPLEXED VANADIUM FOR THE TREATMENT OF DIABETES MELLITUS

[75] Inventors: John H. McNeill, Delta; Hamid R. Hoveyda; Chris Orvig, both of Vancouver, all of Canada

[73] Assignee: The University of British Columbia, Vancouver, Canada

[21] Appl. No.: 767,510

[22] Filed: Sep. 30, 1991

[51] Int. Cl.$^5$ .................. A61K 31/555; A61K 31/28
[52] U.S. Cl. ..................... 514/186; 514/492; 514/884
[58] Field of Search ............... 514/184, 186, 492, 884

[56] References Cited

U.S. PATENT DOCUMENTS 4,882,171  11/1989  Fantus et al. ............... 424/616
5,023,358   6/1991  Lazaro et al. ............... 556/42

OTHER PUBLICATIONS

CA 115:22249h, Komatsu et al., 1990.
Cantley, L. C. Jr, et al., *J. Biol. Chem.* 252: 7421–7423 (1977).
Cantley, L. C. Jr., et al., *J. Biol. Chem.* 254:1781–1784, (1979).
Shechter, Y., *Diabetes* 39:1–5, (1990).
Shechter, Y. et al., *Nature*, (London) 284:556–558 (1980).
Heylinger, C. E. et al., *Science* 227:1474–1477 (1985).
Sakurai, et al., *Biochem. Biophys. Res. Comm.* 96:293–298 (1980).
Ramanadham, S. et al., *Amer. J. Physiol* 257:H904–H911 (1989).
Ramanadham, S. et al., *Metabolism*, 38(10):1022–1028 (1989).
Pederson, R. A. et al., *Diabetes* 38:(11):1390–1395 (1989).
Ramanadham, S. et al., *Can. J. Physiol & Pharmacol.* 68:486–491 (1990).
Ramanadham, S. et al., *Biol. Trace Elements* (1991).
Kadota, S. et al., *Biochem. Biophys. Res. Comm.* 147:259–266 (1987).
Kadota, S. et al., *J. Biol. Chem.* 262:8252–8256 (1987).
Habeeb, J. J. et al., *J. Coord. Chem.* 8:27–33 (1978).
Stewart, C. P. et al., *J. Chem. Soc. Dalton Trans.* 1661–1666 (1972).

*Primary Examiner*—Frederick E. Waddell
*Assistant Examiner*—Kimberly R. Jordan
*Attorney, Agent, or Firm*—Cooley Godward Castro Huddleson & Tatum

[57] ABSTRACT

A pharmaceutical composition useful for lowering blood sugar and suppressing appetite in mammals. The composition comprises compounds of a formula selected from $VOL_2$ or $VO(OR)L_2$ in which L is a bidentate monoprotic ligand and R is an organic group. The composition includes a pharmaceutically acceptable carrier. The invention also provides a method of lowering blood sugar and suppressing appetite in a mammal that comprises administering to the mammal a compound of the above formula.

6 Claims, 4 Drawing Sheets

COMPLEXED VANADIUM FOR THE TREATMENT OF DIABETES MELLITUS

FIELD OF THE INVENTION

This invention relates to a pharmaceutical composition useful for lowering blood sugar and suppressing appetite in a mammal, and to a method of lowering blood glucose and suppressing appetite using the pharmaceutical composition.

DESCRIPTION OF THE PRIOR ART

Diabetes is a mammalian condition in which the amount of glucose in the blood plasma is abnormally high. The condition can be life-threatening and high glucose levels in the blood plasma (hyperglycemia) can lead to a number of chronic diabetes syndromes, for example, atherosclerosis, microangiopathy, kidney disorders, renal failure, cardiac disease, diabetic retinopathy and other ocular disorders including blindness.

It is a disease of some complexity, as indicated by its effect on a large number of important functions of the body, There are large numbers of sufferers. For example, in the late 1980's over 2.6 million people in the U.S. were diabetics who were taking insulin daily. Approximately an equal number of diabetics were taking oral hypoglycemic agents and another 2 to 3 million people were controlling the disease by dietary methods alone. It is estimated there are several million people who are undiagnosed diabetics.

In non-diabetics plasma glucose level is maintained automatically in a complex procedure that involves, inter alia, the hormone insulin. In diabetics, external intervention is needed. Treatment of diabetes is now carried out using several drugs. Insulin is the mainstay of treatment; it replaces the natural hormone produced in the pancreas. In diabetes, insulin is not produced in sufficient quantities, or the body becomes resistant to insulin and requires more than normal amounts to produce the necessary effect.

Insulin must be given by injection. Insulin cannot be administered orally as it is decomposed before or during passage through the gastrointestinal tract. It is difficult to determine the exact amount required This can result in overdoses, leading to hypoglycemia, and to inadequate doses, leading to poor control of the disease and the development of secondary complications.

Oral diabetes medications are available. Sulfonylureas depend on insulin release in the body and are therefore not effective in patients who cannot make their own insulin. As with insulin it can be difficult to obtain the correct dose. The biguanide compounds lower blood glucose, but can produce side effects. These side effects include lactic acidosis, which can be fatal.

The compound sodium orthovanadate was found by Cantley and co-workers to be a potent inhibitor of $Na^+$-$K^+$ ATPase (1). The same group showed that vanadate (vanadium+5) taken up by the red blood cells was reduced to vanadium +4 in the form of vanadyl ion $V=O^{2+}$ in the cytoplasm (2).

Since the above work, there has been a significant focus on the effects of vanadium, mostly as vanadate, on glucose metabolism and uptake into cells. A natural outgrowth of this work has been the study of vanadium and diabetes (3).

The insulin-like effect of vanadate ion ($VO_4^{3-}$) in vitro has been known since 1980 (4) and is currently under investigation. In the 1980 paper, it was shown that the insulin-like stimulation of glucose oxidation in rat adipocytes was due to the vanadyl ion. In 1985, McNeill et al. reported that vanadate, when administered in drinking water, decreased the elevated blood glucose and prevented the depression of cardiac performance in rats made diabetic with streptozotocin (STZ) Subsequently, there has been a burgeoning interest in the insulin-mimetic effects of vanadate and vanadyl since Sakurai et al. showed that vanadate is reduced in vivo to vanadyl (6). Drawbacks to vanadate are that it is poorly absorbed from the gastrointestinal tract to the blood and that it is toxic. Administered concentrations must be close to the toxic level, if the insulin-mimetic effects in animals are to be achieved.

Subsequent work by McNeill et al. (7, 8, 9, 10, 11) has shown that vanadyl administered orally as vanadyl sulfate will also lower blood glucose and blood lipids in STZ diabetic rats and will prevent secondary complications of diabetes such as cataracts and cardiac dysfunction. Vanadyl sulfate is less toxic than the vanadate form of vanadium but is also poorly absorbed There have only been two attempts to modify the biological uptake of vanadium by changing the chemical form in which it is supplied from either vanadate ($VO_4^{3-}$) or vanadyl sulfate ($VOSO_4.(H_2O)_x$), which has been used because the active form of vanadium may be the vanadyl ion. Work on vanadium peroxides has been carried out by Posner et al. (12,13) and U.S. Pat. No. 4,882,171 to Fantus and Posner was issued on Nov. 21, 1989. It relates to vanadium-peroxide compositions as insulin mimics. This work involves in vitro studies of co-administered vanadate and peroxide.

European patent 305,264 issued Mar. 1, 1989 to Lazaro et al. describes and claims a vanadyl cysteine compound for the oral treatment of diabetes. The compound in the European patent has the structure:

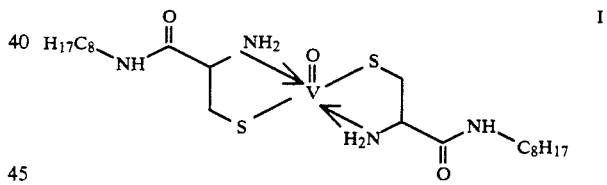

The direct electrochemical preparation of a vanadyl maltol compound was reported in 1978 (14). The biological activity was not examined and the structural formula was not determined but was suggested to be:

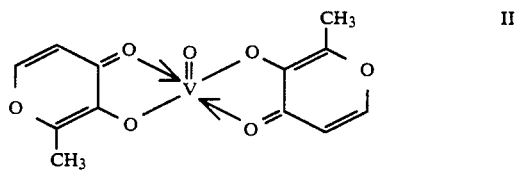

Its electron paramagnetic resonance spectrum was reported in 1972 (15) and again in 1987 (16). Alkoxo-oxovanadium (V) derivatives of the maltolate anion have been known since the 1960's (17), but again the biological activity was not examined.

SUMMARY OF THE INVENTION

There is a need for medication, preferably to be taken orally, that is effective in the treatment of diabetes Accordingly, the present invention provides a pharmaceutical composition useful for lowering blood sugar and depressing appetite in a mammal, the composition comprising a vanadium compound of the formula:

$VOL_2$ or $VO(OR)L_2$ in which
L is a bidentate monoprotic ligand; and
R is an organic group,
in combination with a pharmaceutically acceptable carrier.

The bidentate monoprotic ligand may be, for example, a hydroxamate, 2,4-dione, alpha-hydroxypyrone, alpha-hydroxypyridinone, or other bidentate monoprotic group. All the above compounds have an overall neutral charge and should undergo significant gastrointestinal absorption.

Preferably, the vanadium compound has a structure selected from:

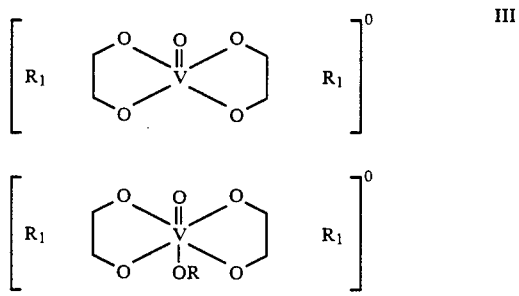

in which R is as defined above and $R_1$ is the balance of the bidentate monoprotic ligand.

A preferred compound is bis(maltolato)oxovanadium(IV) having structural formula II set out above.

The present invention is also a method of lowering blood sugar in a mammal that comprises administering to the mammal a vanadium compound of the general formula:

$VOL_2$ or $VO(OR)L_2$ in which
L is a bidentate monoprotic ligand; and
R is an organic group, Again, the preferred compounds are those of general formula III and, particularly, the compound of formula II above.

The invention is also a method for suppressing appetite in a mammal that comprises administering to the mammal a compound of the general formula:

$VOL_2$ or $VO(OR)L_2$ in which
L is a bidentate monoprotic ligand; and
R is an organic group,
in combination with a pharmaceutically acceptable carrier.

As above, the preferred compounds are those of general formula III and, in particular, the compound of formula II.

The following examples illustrate the invention but are not intended to limit the invention.

EXPERIMENTAL SECTION

Compound Preparation

The compound bis(maltolato)oxovanadium(IV) was prepared nearly quantitatively by combining maltol (3-hydroxy-2-methyl-4-pyrone) and vanadyl sulfate in hot or boiling water at a ratio of 2 to 1. The pH of the solution was raised to 8.5 and the solution was refluxed overnight. The product was a deep purple-green compound that precipitated and was filtered after cooling the reaction mixture to room temperature. The compound is birefringent.

The compound is characterized as follows:

Its elemental analysis is correct for $C_{12}H_{10}O_7V$; % calculated (found): C 45.45 (45.60): H 3.18 (3.30) and its electron impact mass spectrum is also consistent: $m/e = 317$ ($M^+$). The infrared spectrum shows absorptions (KBr disk) characteristic of the maltolato anion bound to a metal cation (1610, 1570, 1560, 1465 cm$^{-1}$) and characteristic of the vanadyl group $V=O$ (995 cm$^{-1}$). It has a magnetic moment in the solid state of 1.76 B.M. indicating one unpaired electron; however, it gives a clear $^1H$ NMR spectrum in $D_2O$ or $d_4$-methanol ($\delta 2.5(s,6H)$, $6.55(d,2H)$, $8.15(d,2H)$) and a clear $^{51}V$ NMR spectrum in $D_2O$(-496 ppm). The compound is quite water-soluble (about 7 mM, 2mg mL$^{-1}$)

Pharmacological Experiments

The following experiments were conducted with bis(maltolato)oxovanadium (IV), as prepared above.

Initial experiments were carried out to determine pharmacological effectiveness of the compound. Using male rats, made diabetic by the injection of STZ at a dose of 60 mg/kg i.v., the compound was initially given by intraperitoneal (i.p.) injection as a suspension in 1% methyl cellulose.

1. Injection.

Nine out of the twelve rats given 15 mg/kg i.p (0.05 mmol/kg) responded to the compound with a decrease in blood glucose. Two animals developed hypoglycemia.

2. Oral Administration.

a. Drinking. Administration of the vanadyl compound in the drinking water at doses of 0.46–0.92 mmol/kg (150–300 mg/kg, using concentrations of 0.5–1.3 mg/mL) reduced blood glucose in four diabetic rats into the normal range. Fluid intake was also decreased to normal in these animals.

b. Gavage. Six out of six diabetic rats responded to the vanadyl compound with a decrease in blood glucose when the compound was given by gavage in a dose of 160 μmol/kg over 40 days. The peak fall in blood glucose occurred 5 hours after administering the drug. The blood glucose returned to diabetic levels usually within 12 hours.

Based on these preliminary studies, more detailed studies were undertaken to determine the minimum effective dose of the compound required to maintain normal blood glucose in diabetic animals.

Prolonged Administration

Bis(maltolato)oxovanadium(IV) was administered to normal and diabetic rats in drinking water.

The study was composed of 4 groups of animals. Control (8 animals) Control-Treated (11 animals), Diabetic (11 animals) and Diabetic-Treated (12 animals). The diabetic state was induced by injecting STZ at 60 mg/kg dissolved in 0.9% NaCl I.V. via the tail vein to anaesthetised rats. The two control groups were injected with 0.9% NaCl I.V. through the tail vein. The diabetic state was determined with a "Testape" TM test at 3 days post-injection and later confirmed with a glucometer test. Blood glucose and insulin assays were carried out post-injection over the course of the study. Treatment according to the invention was started 1 week after determination of the diabetic state.

Treated diabetic animals received between 0.3 and 0.5 mmol/kg of the compound/day in drinking water over a 77 day period. Treated control animals received a slightly lower dose (0.2–0.3 mmol/day) over the same period. The concentration of compound in the drinking water was varied between 1.6 and 3.2 mM. The reason for the differing doses in the two sets of animals is that the two groups drank different amounts of water daily; it was difficult to attain the same dose in both groups.

BRIEF DESCRIPTION OF THE DRAWINGS

The results are, in part, set out graphically in the drawings in which.

Figure 1:
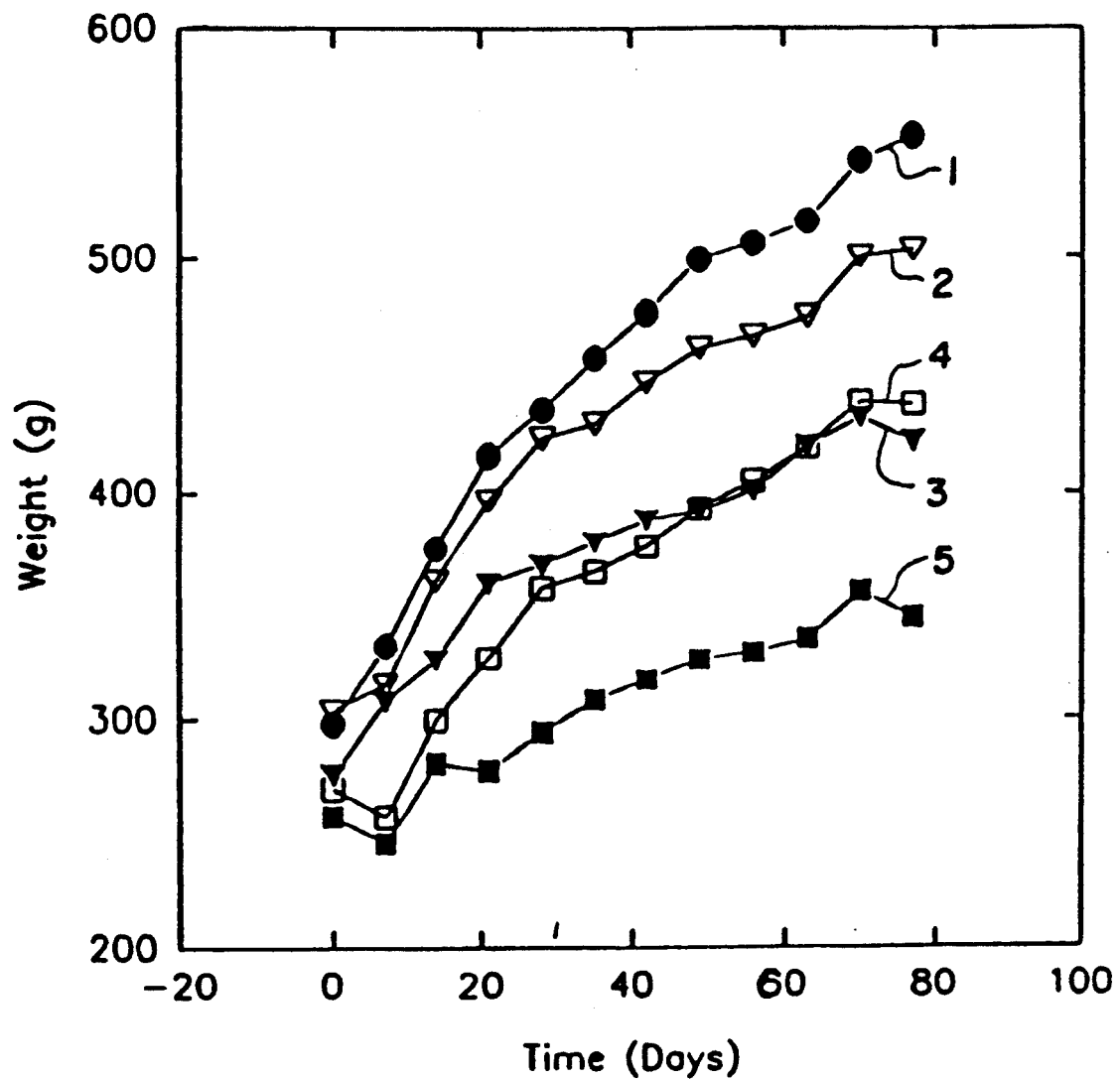
FIG. 1 relates change in weight with time.

With the above treatment regimen, the following was noted:

1. The weight gain over the 77 day period is shown in FIG. 1. As indicated above 4 groups of animals were studied, but the diabetic-treated group was sub-divided to diabetic-treated responders (8 animals) and diabetic-treated non-responders (4 animals). Curve 1 is the control group, curve 2 the control-treated group, curve 3 the diabetic group, curve 4 is the diabetic-treated responders and curve 5 is the diabetic-treated non-responders. Initially, there was a significant difference only between the two control groups with respect to the three diabetic groups. However, by day 7 there was a significant difference between the two diabetic-treated groups with respect to all other groups. By day 28, the diabetic-treated non-responder group was significantly different from the other 4 groups and there was no longer a significant difference between the diabetic group and the diabetic responder group. By day 56, there was a significant difference between the control group and the control treated group. Treatment began with a 3.17 mM solution of the compound. On day 6, the concentration was reduced to 1.58 mM (0.5 mg/ml). On day 24, the concentration was increased to 2.37 mM (0.7 mg/ml). At this point 8 out of the 12 animals were responding to the compound.

The control treated animals showed a significantly decreased weight gain beginning at day 56. The decrease was correlated with the decrease in food intake.

Figure 2:
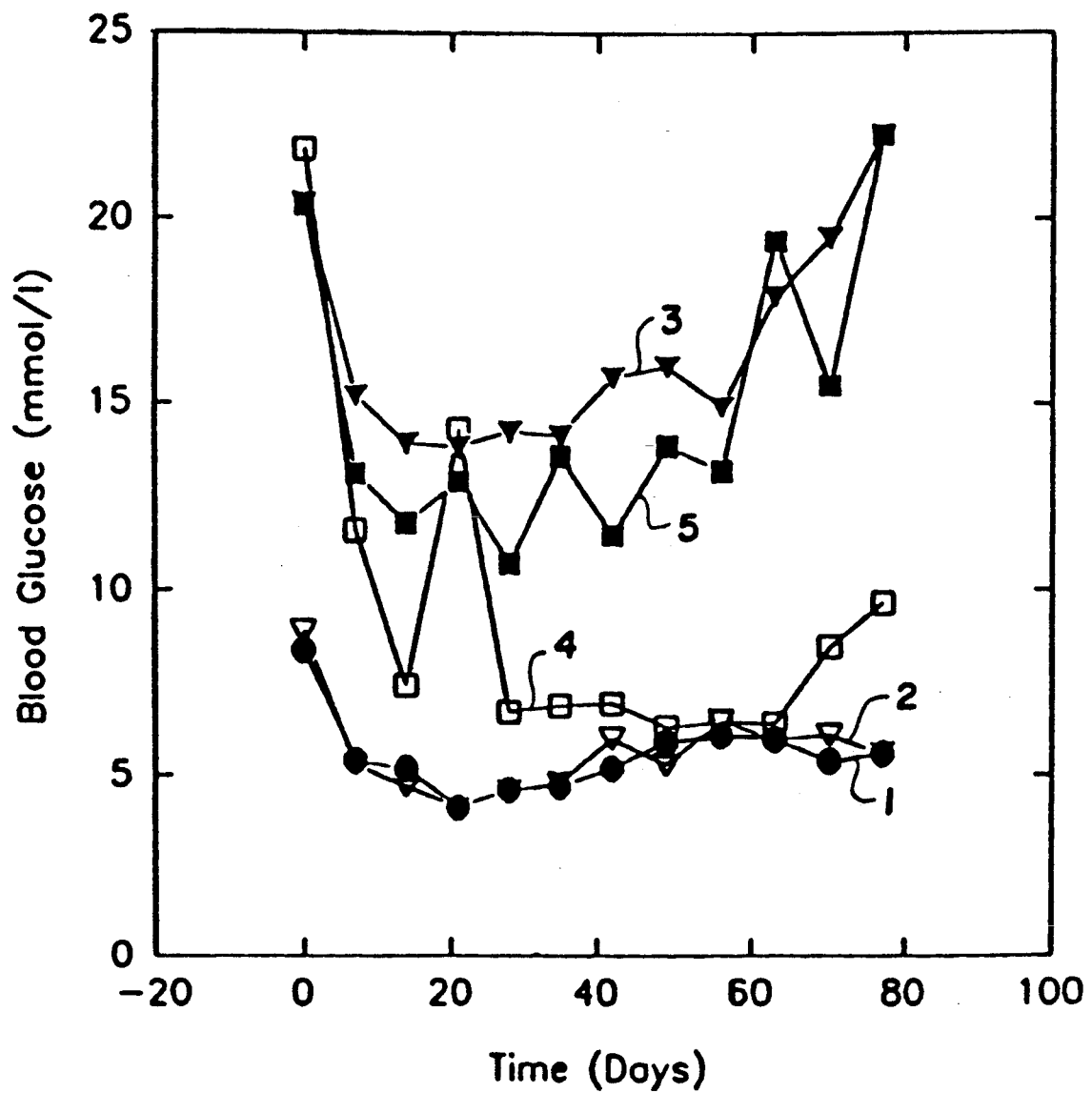
FIG. 2 shows average blood glucose values in mmol/1 (over time)

2. FIG. 2 shows average blood glucose values (mmol/1) for the 5 groups based on weekly blood glucose determinations. The 5 groups were as in FIG. 1. Initially, there was a significant difference between the two control groups with respect to all three of the diabetic groups. By day 7, there was a significant difference between the diabetic group with respect to both diabetic-treated groups. By day 14, the diabetic-treated responder group was euglycemic; however, on day 18 there was an increase in blood glucose levels for this group due to the necessity to withhold treatment for a few days to treat hypoglycemia, which developed in several animals. The diabetic-treated non-responder group consists of rats which exhibited marked fluctuations in glucose values.

Thus, eight of the twelve treated diabetic rats had their blood glucose values lowered from 20+mM to less than 10 mM from day 7 onwards. Four of the twelve rats had blood glucose readings ranging from 6–20mM on any given day. These rats are the non-responders. By day 24, diabetic rats that responded to the compound had normal blood glucose.

Figure 3:
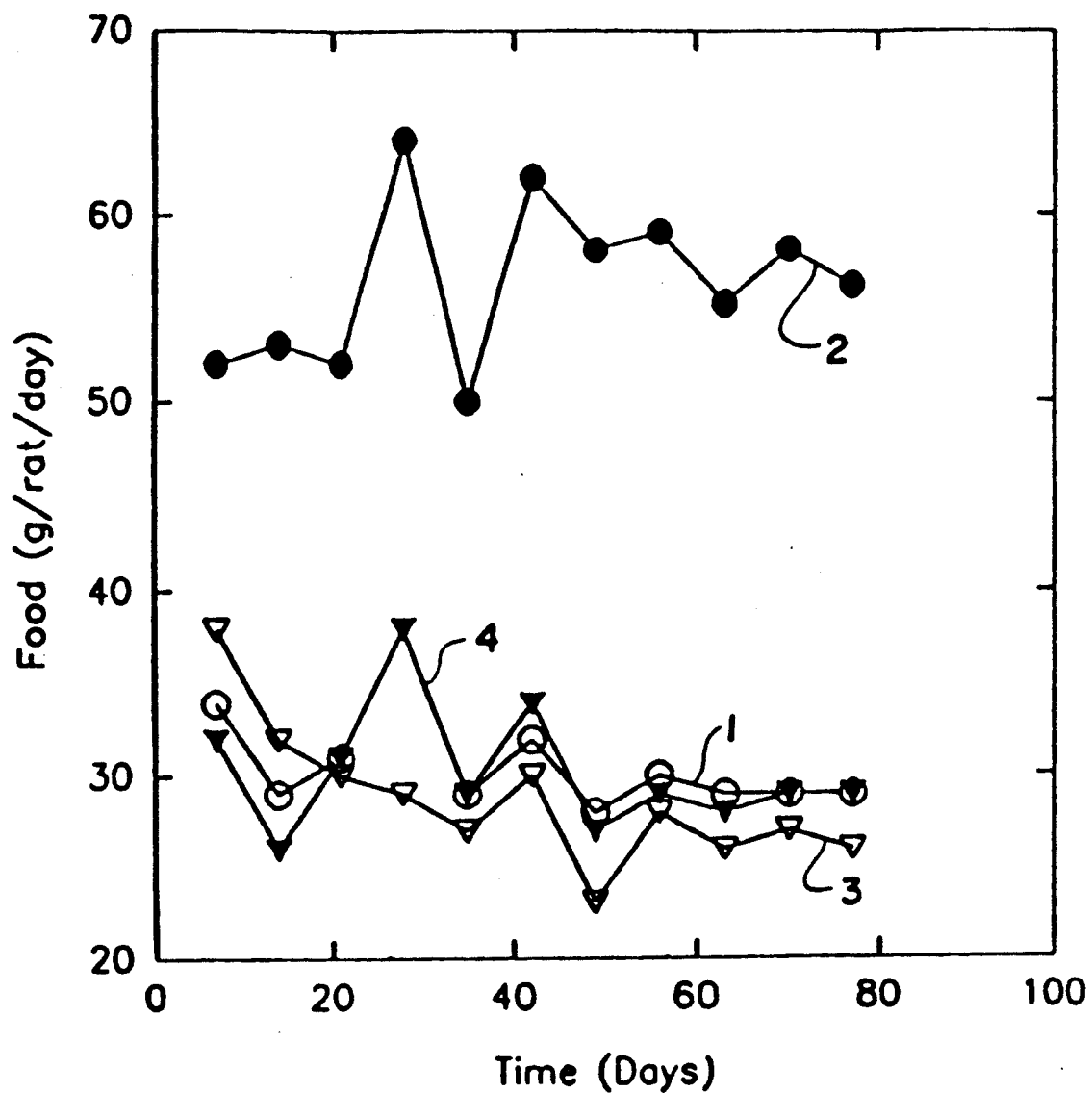
FIG. 3 shows the daily food consumption.

3. FIG. 3 demonstrates the daily food consumption per rat. The rats were allowed free access to food with 2–3 rats per cage for the four treatment groups. The control group is curve 1 the diabetic group is curve 2 the control-treated group is curve 3 and the diabetic-treated group is curve 4. For the first approximately 50 days of treatment, the only significant difference occurred between the diabetic group with respect to all of the other groups. However, from day 63 on, there was also a significant difference between the control-treated group and all the other groups. There was no significant difference between the control and the diabetic-treated groups at any time.

Figure 4:
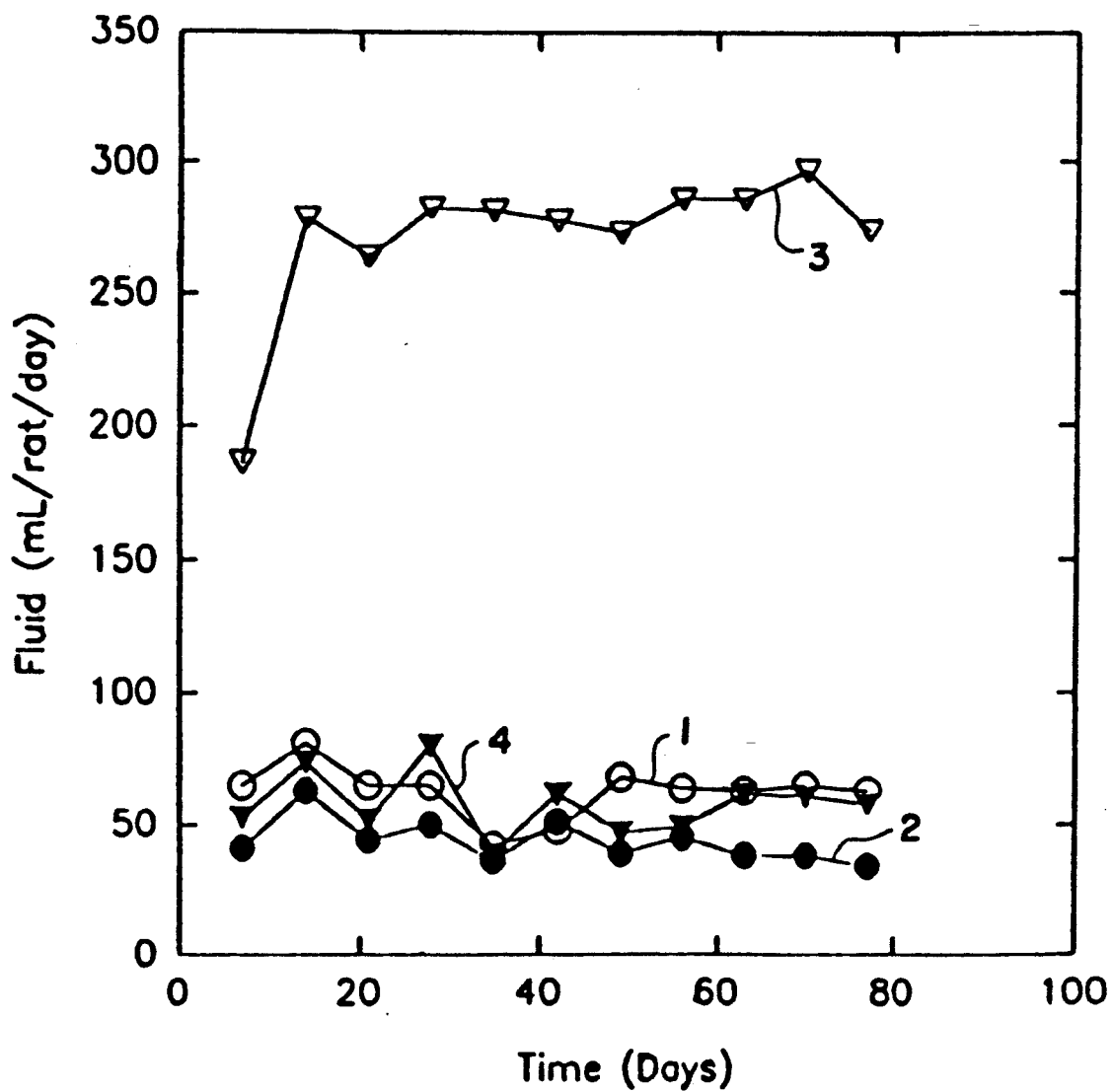
FIG. 4 shows daily fluid consumption.

FIG. 4 shows the daily fluid consumption per rat. The rats had free access to fluids with 2–3 rats per cage for the four treatment groups. The control group is curve 1, the control-treated group is curve 2, the diabetic group is curve 3 and the diabetic-treated group is curve 4. Initially, the only significant difference occurred between the diabetic group with respect to all of the other treatment groups. However by day 63, there was also a significant difference between the control treated group and all the other treatment groups. There was no significant difference in fluid consumption between the control and the diabetic-treated groups throughout.

FIGS. 3 and 4 illustrate that control of blood glucose was accompanied by a reduction in food intake in the diabetic rats from greater than 50 grams per day to about 30 grams per day (28±1.6 on day 77). There was a slight reduction in food intake (from 29 ±0.1 to 25.5 ±0.3) in control rats treated with the compound. Fluid intake fell from about 275 ml/rat in the diabetic group to about 60 ml/rat in the diabetic treated group. There was also a decrease in fluid intake in the control treated group compared with control rats (62.7 ±7.4 vs 33.6 ±7.2 ml on day 77). As stated above, the decrease in food and water intake correlates with the decrease in weight gain in control animals.

4. Treatment with the compound decreased weight gain in control animals (200 g vs 250 g for control over the 77 day period). Diabetic-treated animals gained almost exactly the same weight (140 g) as diabetics, despite the decrease in food intake; thus weight gain in diabetic-treated animals lagged behind that of control groups animals.

5. Insulin values in control treated rats decreased to the same value as those for diabetic animals (approximately 22 $\mu$U/ml) and were significantly lower than those of control 35.8 ±1.2 $\mu$U/ml) as shown in Table 1:

TABLE I

| Insulin Values, μU/ml (Day 28 of vanadyl bis(maltolato) Study) | | | |
|---|---|---|---|
| Control | Control-Treated | Diabetic | Diabetic-Treated |
| 35.8 ± 1.2 | 21.6 ± 1.2 | 21.4 ± 2.6 | 22.0 ± 1.6 |

6. Plasma triglyceride and cholesterol values in diabetic animals were restored to control values by treatment with the drug as shown in Table 2:

TABLE 2

Lipid Values in Vanadyl bis(maltolato) Study

| | Control | Control Treated | Diabetic-Treated Responders | Diabetic-Treated Non-Responders | Diabetic |
|---|---|---|---|---|---|
| *Cholsterol mmol/l Means ± S.E.M.* | | | | | |
| Pretreatment (Day before treatment started) | 1.40 ± 0.03 (8) | 1.64 ± 0.08 (8) | 1.67 ± 0.10 (7) | 1.51 ± 0.07 (4) | 1.58 ± 0.10 (11) |
| Week 6 | 1.37 ± 0.06 (8) | 1.60 ± 0.06 (10) | 1.58 ± 0.11 (8) | 1.48 ± 0.09 (4) | 2.65 ± 0.28* (11) |

*Diabetic untreated is significantly different from all other groups by ANOVA followed by either Fishers', Newman-Keuls' or Duncans' test.

| | | | Triglyceride mmol/l Means ± S.E.M. | | |
|---|---|---|---|---|---|
| Pretreatment (Day before treatment started) | 1.27 ± 0.08 (8) | 1.21 ± 0.14 (8) | 1.10 ± 0.09 (8) | 1.85 ± 0.41* (4) | 1.21 ± 0.08 (11) |

*Diabetic-treated nonresponders are significantly different from all other groups by ANOVA followed by either Fishers', Newman-Keuls' or Duncans' test.

| | | | | | |
|---|---|---|---|---|---|
| Week 6 | 1.81 ± 0.11 (8) | 2.04 ± 0.22 (10) | 1.70 ± 0.18 (8) | 2.31 ± 0.19 (4) | 4.14 ± 0.98* (11) |

*Diabetic-untreated are significantly different from all groups except diabetic-treated nonresponders by ANOVA followed by Fishers' and Duncans' test, but not by ANOVA followed by Newman-Keuls' test. One rat in this group has a very high triglyceride value - 13.1 mmol/l.

7. At the end of 77 days of treatment, 0/8 of the treated diabetic rats, which were controlled by the drug, had cataracts. 5/11 Of the untreated diabetic animals showed cataracts. One of the four treated animals, not controlled by the drug, also had a cataract. The first cataract developed at 60 days in the untreated diabetic group.

The present invention provides a pharmaceutical composition useful for the treatment of diabetes mellitus, or an appetite suppressant, or both. The active compounds are absorbed across the gastrointestinal barrier and deliver the vanadyl ion to the bloodstream, where the insulin-mimetic properties of vanadium can be expressed. In contrast to insulin, the compositions are active when taken by mouth, and represent a significant advance in diabetes therapy. The compositions are also useful as orally active appetite suppressants and would be effective in treating obesity. The majority of diabetics are overweight, but obesity in general is a significant problem in western society, leading to an increase in morbidity and mortality. A drug that will suppress appetite, leading to weight loss, is of significant value. The active ingredients of the present invention are simple, monomeric species in the solid state. They are easily prepared, easily administered, and highly effective both in lowering blood glucose and in suppressing appetite.

REFERENCES

1. Cantley, L.C. Jr. et al. "Vanadate is a potent (Na,K)-ATPase inhibitor found in ATP derived from muscle." J. Biol. Chem. 252:7421-7423, 1977.
2. Cantley, L.C. Jr. and Aisen, P. "The fate of cytoplasmic vanadium implications on (Na,K)-ATPase inhibition." J. Biol. chem. 254:1781-1784, 1979.
3. Reviewed in Shechter, Y. "Insulin-mimetic effects of vanadate: possible implications for future treatment of diabetes " Diabetes 39:1-5, 1990.
4. Shechter, Y. and Karlish, S.J.D. "Insulin-like stimulation of glucose oxidation in rat adipocytes by vanadyl(IV) ions." Nature (London). 284:556-558, 1980.
5. Heyliger, C.E., Tahiliani, A.G. and McNeill, J.H. "Effect of vanadate on elevated blood glucose and depressed cardiac performance of diabetic rats." Science. 227:1474-1477,1985.
6. Sakurai et al. "Detection of oxovanadium(IV) and characterization of its ligand environment in subcellular fractions of the liver of rats treated with pentavalent vanadium(V)." Biochem. Biophys. Res. Comm. 96:293-298,1980.
7. Ramanadham, S., Mongold, J.J., Brownsey, R.W., Cros, G.H. and McNeill, J.H. "Oral vanadyl sulfate in treatment of diabetes mellitus in rats". Amer. J. Physiol. 257:H904-H911, 1989.
8. Ramanadham, S., Brownsey, R.W., Cros, G.H., Mongold, J.J. and McNeill, J.H. "Sustained prevention of myocardial and metabolic abnormalities in diabetic rats following withdrawal from oral vanadyl treatment" Metabolism 38(10):1022-1028, 1989.
9. Pederson, R.A., Ramanadham, S., Buchan, A.M.J. and McNeill, J. "Long term effects of vanadyl treatment on streptozotocin-induced diabetes in rats". Diabetes 38(11):1390-1395, 1989.
10. Ramanadham, S., Cros, G.H., Mongold, J.J., Serrano, J.J., and McNeill, J.H. "Enhanced in vivo sensitivity of vanadyl-treated diabetic rats to insulin " Can J. Physiol. & Pharmacol. 68:486-491,1990.
11. Ramanadham, S., Heyliger, C., Gresser, M.J. Tracey, A.S. and McNeill, J.H. "The distribution and half-life for retention of vanadium in the organs of normal and diabetic rats orally fed vanadium(IV) and vanadium(V)." Biol. Trace Elements (in press) 1991.
12. Kadota, S. et al. "Peroxide(s) of vanadium a novel and potent insulin-mimetic agent which activates the insulin receptor kinase " Biochem. Biophys. Res. Comm. 147:259-266,1987.
13. Kadota, S. et al. "Stimulation of insulin-like growth factor II receptor binding and insulin receptor kinase activity in rat adipocytes: effects of vanadate and $H_2O_2$." J. Biol. Chem. 262:8252-8256, 1987.

14. Habeeb, J.J., Tuck, D.G. and Walters, F.H. "Direct electrochemical synthesis of some metal chelate complexes." J. Coord. Chem. 8:27–33, 1978
15. Stewart, C.P. and Porte, A.L. "Electron paramagnetic resonance spectra of some oxovanadium(IV) chelates."
16. Bechmann, W., Uhlemann, E., Kirmse, R. and Kohler, K. "EPR-Untersuchungen an vanadylkomplexen." Z. Anorg. Allg. Chem. 544:215–224,1987.
17. Jungnickel, J.E. and Klinger, W. "Photometrische bestimmung von vanadium mit 2-methyl-3-hydroxy--pyron(maltol)." Z. Anal. Chem. 203:257–260, 1964.

We claim:

1. A pharmaceutical composition comprising an effective amount of bis(maltolato)oxovanadium(IV) having the formula:

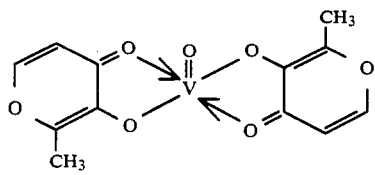

II in combination with a pharmaceuticaly acceptable carrier.

2. A composition as claimed in claim 1 in which the concentration of the bis(maltolato)oxovanadium(IV) is sufficient to provide a concentration in the range of 1.6 to 3.2mM.

3. A composition as claimed in claim 1 in which the carrier is aqeuous methyl cellulose containing about 1% methyl cellulose.

4. A method of lowering blood sugar in a mammal that comprises administering to the mammal an effective amount of bis(maltoalto)oxovanadium(IV) having the formula:

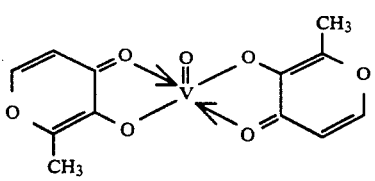

II

5. A method as claimed in claim 1 in which the bis(-maltotao)oxovanadium(IV) is administered by injection at a dose of about 15 mg/kg.

6. A method as claimed in claim 4 in which the bis(-maltolato)oxovanadium(IV) is administered orally at a dose in the range of 150–300 mg/kg.

* * * * *